United States Patent
Sauer et al.

(10) Patent No.: US 8,375,976 B2
(45) Date of Patent: Feb. 19, 2013

(54) METHOD AND DEVICE FOR ATTENUATING PRESSURE SURGES OF LIQUIDS FLOWING INSIDE A LIQUID CONDUIT

(75) Inventors: Klaus Sauer, Rieschweiler-Muhlbach (DE); Gilbert Moser, Graz (AT)

(73) Assignee: Volker Moser, Graz (AT)

( * ) Notice: Subject to any disclaimer, the term of this patent is extended or adjusted under 35 U.S.C. 154(b) by 1859 days.

(21) Appl. No.: 10/507,982

(22) PCT Filed: Mar. 12, 2003

(86) PCT No.: PCT/AT03/00072
§ 371 (c)(1),
(2), (4) Date: Mar. 28, 2005

(87) PCT Pub. No.: WO03/078083
PCT Pub. Date: Sep. 25, 2003

(65) Prior Publication Data
US 2005/0161096 A1    Jul. 28, 2005

(30) Foreign Application Priority Data

Mar. 15, 2002  (AT) .................................. A 399/2002

(51) Int. Cl.
*F04F 1/18*    (2006.01)
(52) U.S. Cl. ....................................... 137/207; 137/240
(58) Field of Classification Search ................. 137/207, 137/240; 138/30; 251/326, 117
See application file for complete search history.

(56) References Cited

U.S. PATENT DOCUMENTS

| | | | | |
|---|---|---|---|---|
| 136,746 A * | 3/1873 | McMahon | .................... | 251/117 |
| 1,829,818 A * | 11/1931 | Agee | .............................. | 137/207 |
| 2,712,831 A | 7/1955 | Day | | |
| 2,731,984 A * | 1/1956 | Everett | ............................ | 138/30 |
| 2,997,049 A | 8/1961 | Thomas | | |
| 3,242,947 A * | 3/1966 | Mizma | ............................ | 138/30 |
| 3,942,549 A * | 3/1976 | Tobin | ............................ | 137/207 |
| 4,308,095 A * | 12/1981 | Brendemuehl | ............... | 137/207 |
| 4,590,796 A * | 5/1986 | Baatz | ............................ | 137/207 |
| 4,750,523 A * | 6/1988 | Crouse | ............................ | 138/30 |
| 5,386,927 A * | 2/1995 | Janssen | ......................... | 137/240 |
| 5,895,028 A * | 4/1999 | Varady | ............................ | 251/205 |

FOREIGN PATENT DOCUMENTS

| | | |
|---|---|---|
| DE | 19706578 C2 | 8/1999 |
| EP | 0107459 A | 2/1984 |
| EP | 0102215 A | 7/1984 |
| JP | 59133900 A | 1/1984 |

\* cited by examiner

*Primary Examiner* — Craig Schneider
*Assistant Examiner* — Craig J Price
(74) *Attorney, Agent, or Firm* — Kilpatrick Townsend & Stockton LLP

(57) ABSTRACT

A system and a method are provided for attenuating pressure surges of liquids, e.g., of a biologically vulnerable liquid, flowing inside a liquid conduit and for cleaning, in particular sterilizing, the liquid conduit. In particular, the liquid is permitted to swerve, in the event that pressure surges occur, into a gas-filled space communicating with the liquid conduit.

7 Claims, 8 Drawing Sheets

Figure 7
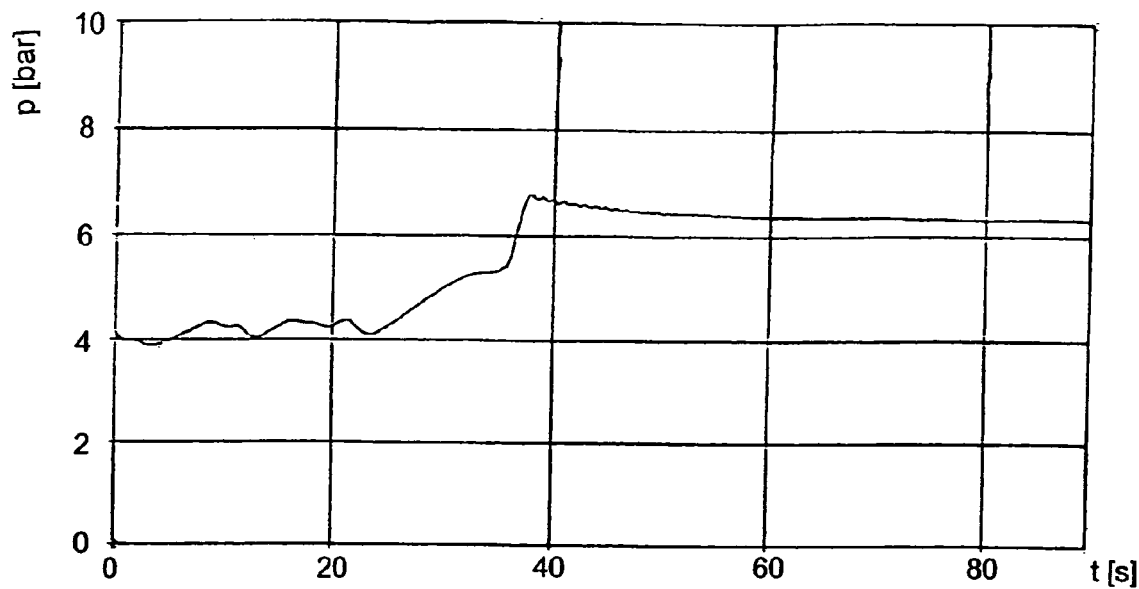
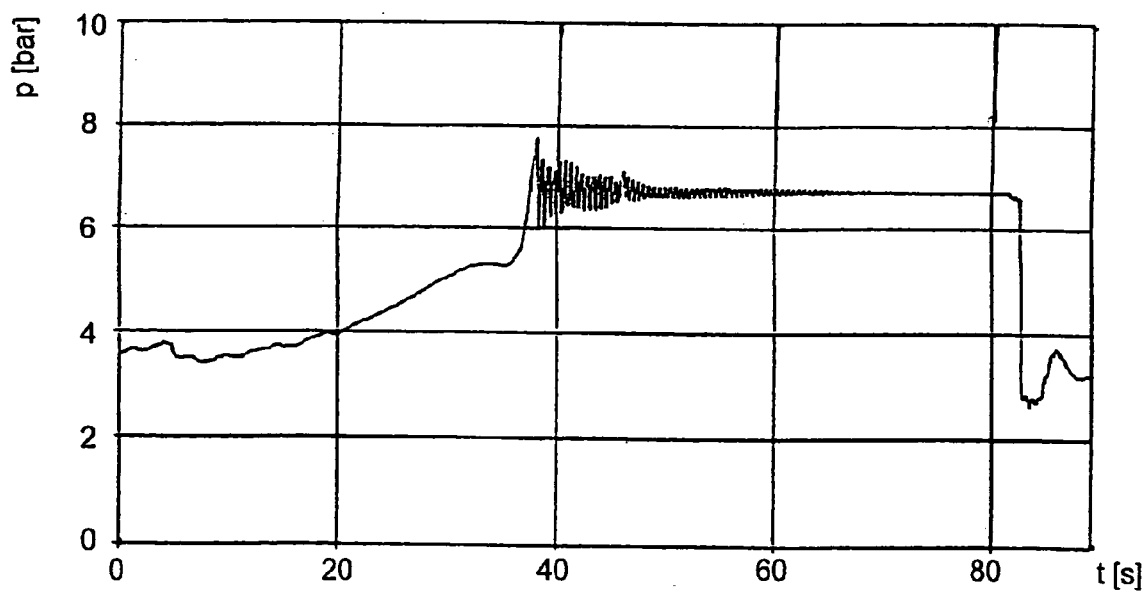
Figure 8

Figure 9
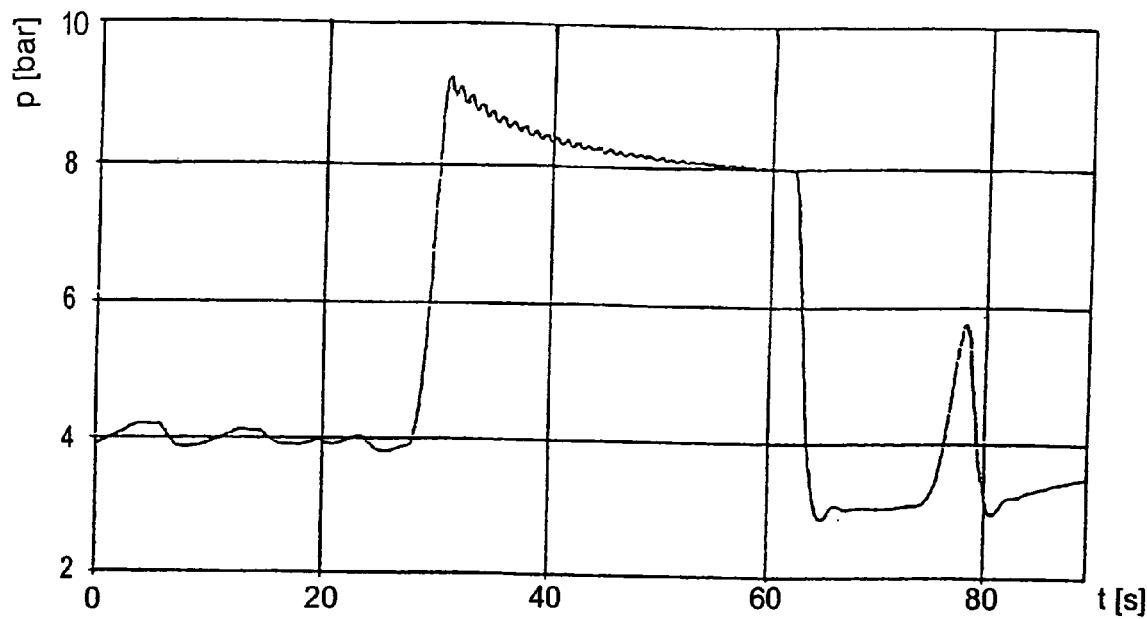
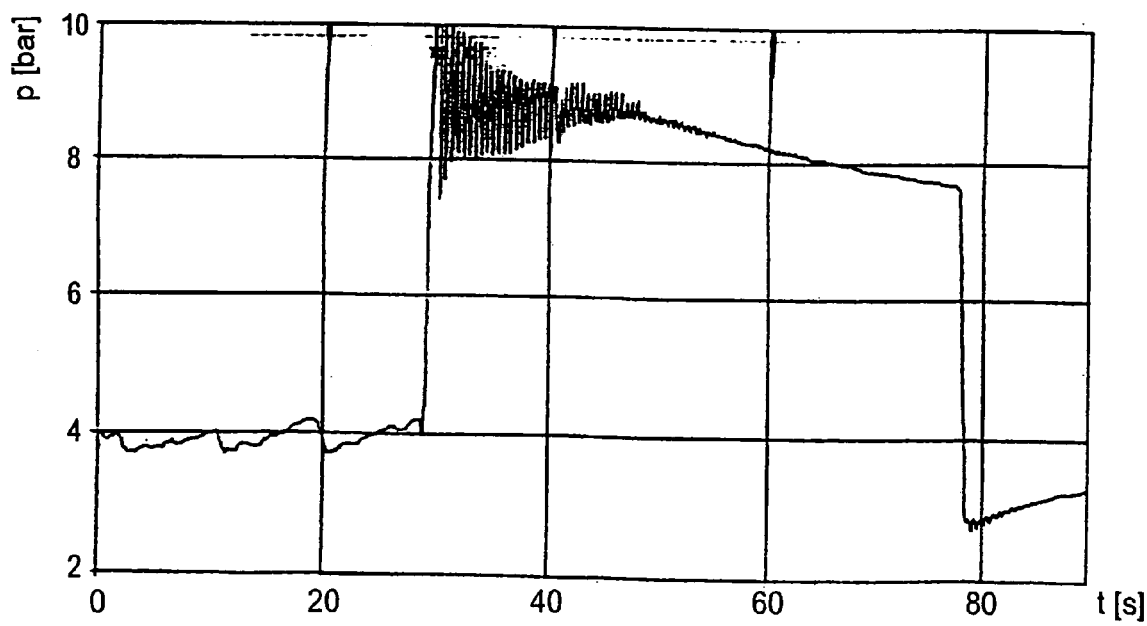
Figure 10

METHOD AND DEVICE FOR ATTENUATING PRESSURE SURGES OF LIQUIDS FLOWING INSIDE A LIQUID CONDUIT

BACKGROUND OF THE INVENTION

The invention relates to a device for attenuating pressure surges of liquids, e.g. of a biologically vulnerable liquid, flowing inside a liquid conduit and for cleaning, in particular sterilizing, the liquid conduit comprising a bypass conduit that bridges over a section of the liquid conduit, wherein an isolating valve as well as a gas supply conduit are provided in the liquid conduit between the outlets of the bypass conduit.

For the transport of liquids through liquid conduits, in particular for the purpose of filling them into containers, the liquids must be brought to particular flow values by means of control and/or check valves in their flow, or the flow of the liquids must be interrupted, respectively, for instance, upon reaching a predetermined filling level in the container. Therefore, pressure variations that are more or less large constantly arise in the liquid conduits. Those variations can be very substantial and in large filling plants, for instance for the bottling of beer, milk, etc., they may exhibit a pulsating characteristic.

Pressure surges can amount to maximum pressures of more than two and a half times the normal liquid-conduit pressure. Thereby, excessive strain is put on the fittings and other appliances such as membrane filters, plate heat exchangers and especially also gaskets. In the case of higher static conduit pressures, such pressure surges must be rated as even more critical in terms of the hypothesis of fatigue strength.

For the purpose of providing a remedy, it is known to use air vessels for attenuating the pressure surges. Such air vessels are indeed a proven and simple attenuation means; however, different pressures in the liquid conduits require differently sized gas spaces in the air vessel which exhibit different characteristic frequencies, which may lead to problems for downstream electronic controls. A further great disadvantage of such air vessels is that cleaning is not possible during an operation cycle. Cleaning an air vessel requires that the same is shut off from the pipeline, whereby, after the cleaning process, the danger that remains of the detergent are present cannot be ruled out. Complete flushing of the air vessel is feasible only in a time-consuming way.

It has also been attempted to attenuate pressure surges with electronic methods, i.e. to provide electronic control and attenuation means. Those, however, depend on the velocity of the sensors and actuators of the system. Nevertheless, especially in high-frequency oscillations, resonances can occur which often aggravate the problem of pressure surges. On the other hand, excess attenuation of the system might also lead to pressure variations which are no longer compensable. In this connection, the occurrence of strongly varying frequencies of the pressure surges constitutes a particular problem.

From utility model document AT 001740 U1, a shunt pipeline, i.e. a bypass conduit, leading to a liquid conduit such as a beer conduit is known, which pipeline is filled with gas in the normal state and serves for the absorption of pressure surges. In that known device, pressure surges might, however, strike through the bypass conduit. Furthermore, it is cumbersome to carry out a purification, in particular involving a sterilization liquid, since, on the one hand, the bypass conduit and, on the other hand, the liquid conduit are to be treated separately, and furthermore a product change will result in difficulties as a result of an inadmissable mixture of the various products successively flowing through the liquid conduit.

SUMMARY OF THE INVENTION

The invention aims at avoiding those disadvantages and difficulties and has as an object to provide a device of the initially described kind which not only enables an excellent attenuation of pressure surges but also a reliable cleaning of the device with simple means so that the application is also provided for biologically vulnerable products such as food products without requiring great efforts. In addition, a product change should also be feasible without substantially mixing the various products.

According to the invention, the object is achieved in that, after the bypass conduit, a throttle is incorporated in the liquid conduit in the flow direction of the liquid.

By means of the throttle it becomes possible to absorb pressure surges and hence to direct the major part of an overpressure into the bypass. That produces a particularly good protection for the means to which the liquid conduit leads such as for filtering installations, filling plants, etc.

A preferred variant of the device according to the invention is characterized in that the bypass conduit is optionally divisible into two gas-filled spaces, preferably two gas-filled spaces of roughly equal volumes, by means of an isolating valve, which both communicate with the liquid conduit for the purpose of attenuating pressure surges.

Thereby, it becomes possible to definitely avoid that liquid flows over the bypass, i.e. to maintain the gas cushion in the bypass in any kind of disturbance. In addition, an optionally provided control valve is prevented from damage. A gas cushion escaping from the bypass and entering the liquid conduit would, for instance, decrease the filtering activity of a filter provided for filtering the liquid, and an indefinable amount of gas would get lost.

Preferably, a pet cock is in each case provided adjacent to the isolating valve and within the section in the bypass conduit that is formed by the isolating valves.

It thereby becomes possible to carry out a product change precisely without cleaning. A product which is different from the previously flowing product reaches the filling station, and is stopped there, whereupon the isolating valves of the bypass conduit are closed and the pet cocks of the bypass conduit are opened until the first product has been discharged completely.

Preferred variants of the device according to the invention are characterized by a combination of the features described herein.

A suitable embodiment is characterized by one lockable gas supply conduit running into the bypass conduit in the flow direction before and another one after the isolating valve dividing the bypass conduit.

Advantageously, the isolating valve provided in the liquid conduit has, in the closed state, a leakage opening enabling a small flow, and suitably the isolating valve provided in the liquid conduit and in the bypass conduit is alternatively operable by means of a control unit.

As the cleaning medium, a sterilization liquid is preferably provided. The device according to the invention is usable to a particularly high degree for biologically vulnerable products, in particular food products.

For securing a liquid level, i.e. in order to prevent the same from rising beyond a predetermined scale, probes for determining a liquid level are preferably provided in the bypass conduit at a predetermined distance from the first and the second isolating valves, with a control unit suitably being provided which is coupled to at least one of the gas supply conduits leading to the bypass conduit so that, if a liquid level is indicated, an automatic gas flushing and hence a discharge of liquid from the bypass conduit will take place.

BRIEF DESCRIPTION OF THE DRAWINGS

The invention is illustrated in greater detail below by way of the drawing in which an exemplary embodiment is shown.

FIGS. 7 to 10 show pressure surges occurring in the liquid conduit as illustrated in chart form, with FIGS. 7 and 9 illustrating pressures experienced with a device made according to the invention and FIGS. 8 and 10 illustrating pressures experienced without a device according to the invention.

DESCRIPTION OF THE PREFERRED EMBODIMENTS

Figure 1:
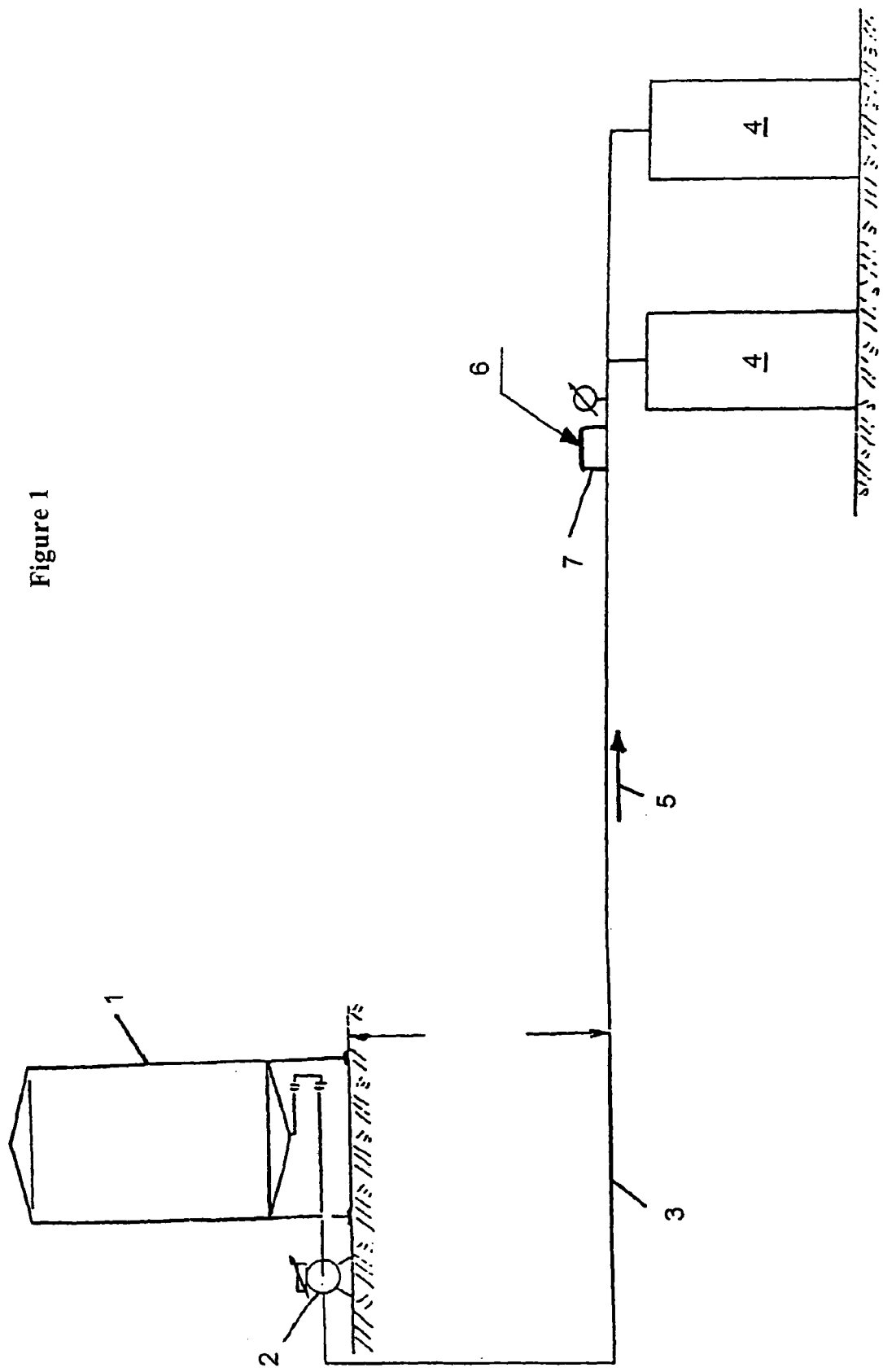
FIG. 1 shows a filling plant for fresh milk in schematic representation.

According to the filling plant for a liquid, herein for fresh milk, as illustrated in FIG. 1, fresh milk passes from a storage tank 1 via a feed pump 2 and a liquid conduit 3 to two filling machines 4 in which milk bottles or other containers such as laminated cardboards, etc. are filled intermittently. A device 6 according to the invention is provided between the fresh milk tank and the filling plant arranged first in the flow direction 5, which device is indicated only schematically in FIG. 1 but is illustrated in detail in FIG. 2. Suitably, the device 6 is incorporated in the liquid conduit right in front of the filling machines 4.

Figure 2:
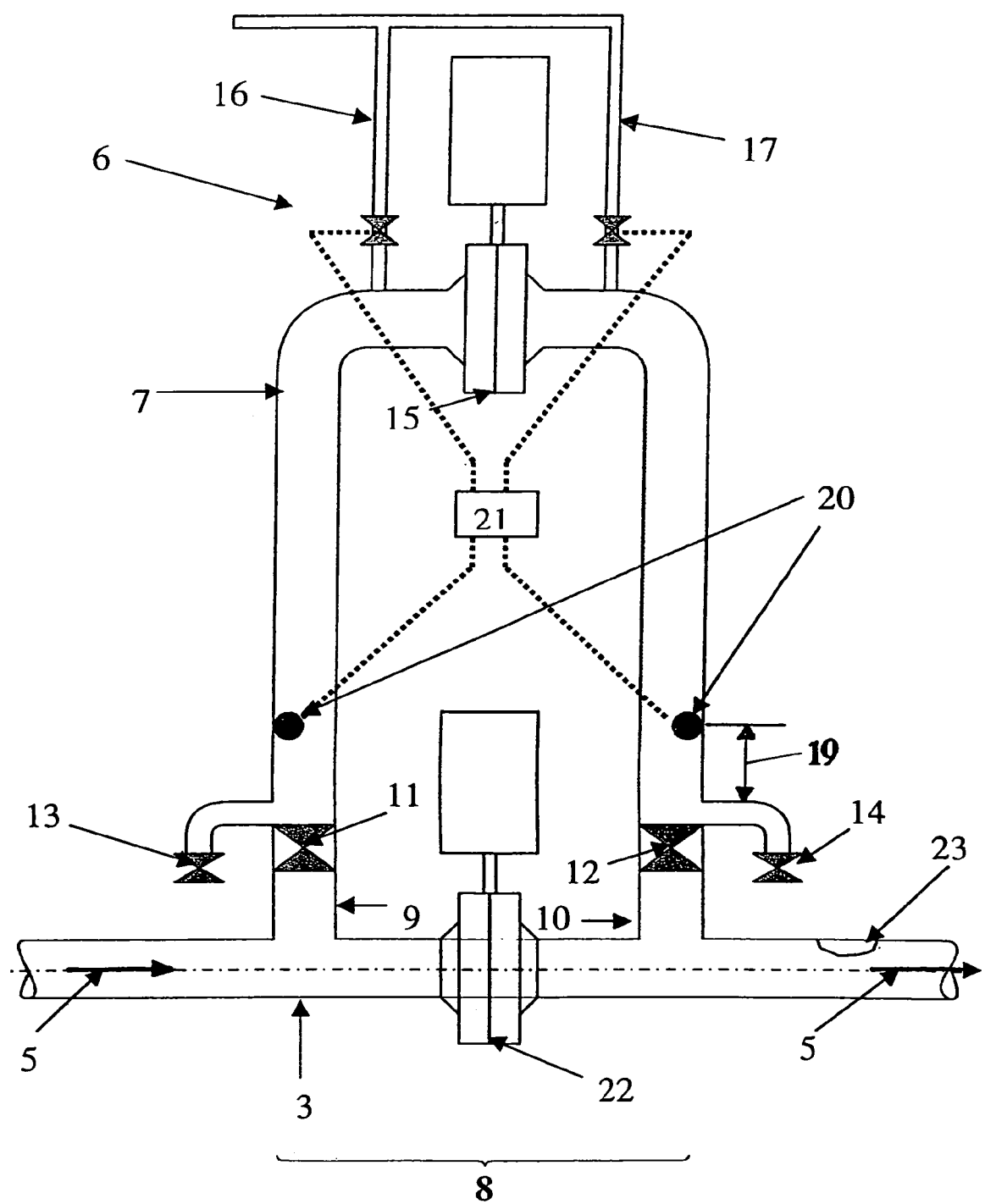
FIG. 2 illustrates the device according to the invention in detail.

According to the embodiment as illustrated in FIG. 2, the device 6 according to the invention exhibits a bypass conduit 7 which bridges over a predetermined section 8 of the liquid conduit 3. In the area where the mouths 9 and 10 of the bypass conduit 7 open into the liquid conduit 3, the bypass conduit 7 is provided with a first and a second isolating valve 11, 12 so that it is possible to separate the bypass conduit 7, with respect to the pipelines, completely from the liquid conduit.

A lockable pet cock 13, 14 is in each case provided in the bypass conduit adjacent to the first and the second isolating valves 11, 12, namely within the section of the bypass conduit 7 formed by the first and the second isolating valves 11, 12. A third isolating valve 15 is located in the bypass conduit 7 at about the same distance from the openings of the bypass conduit 7 (at 9 and 10, respectively) into the liquid conduit 3.

Lockable gas supply conduits 16, 17 running into the bypass conduit 7 are provided in the flow direction 5 of the liquid before and after the third isolating valve 15.

In order to avoid an excessively high liquid level in the bypass conduit 7, probes 20 are provided in the same at a predetermined distance 19 from the first and the second isolating valves, by means of which probes the presence of liquid can be determined at the level of the probes 20. If those probes 20 are flushed over by a liquid, those probes 20 give off a signal which controls, by means of a control unit 21, the influx of a gas via the gas supply conduits 16 or 17 into the respective flooded section of the bypass conduit 7.

Figure 6:
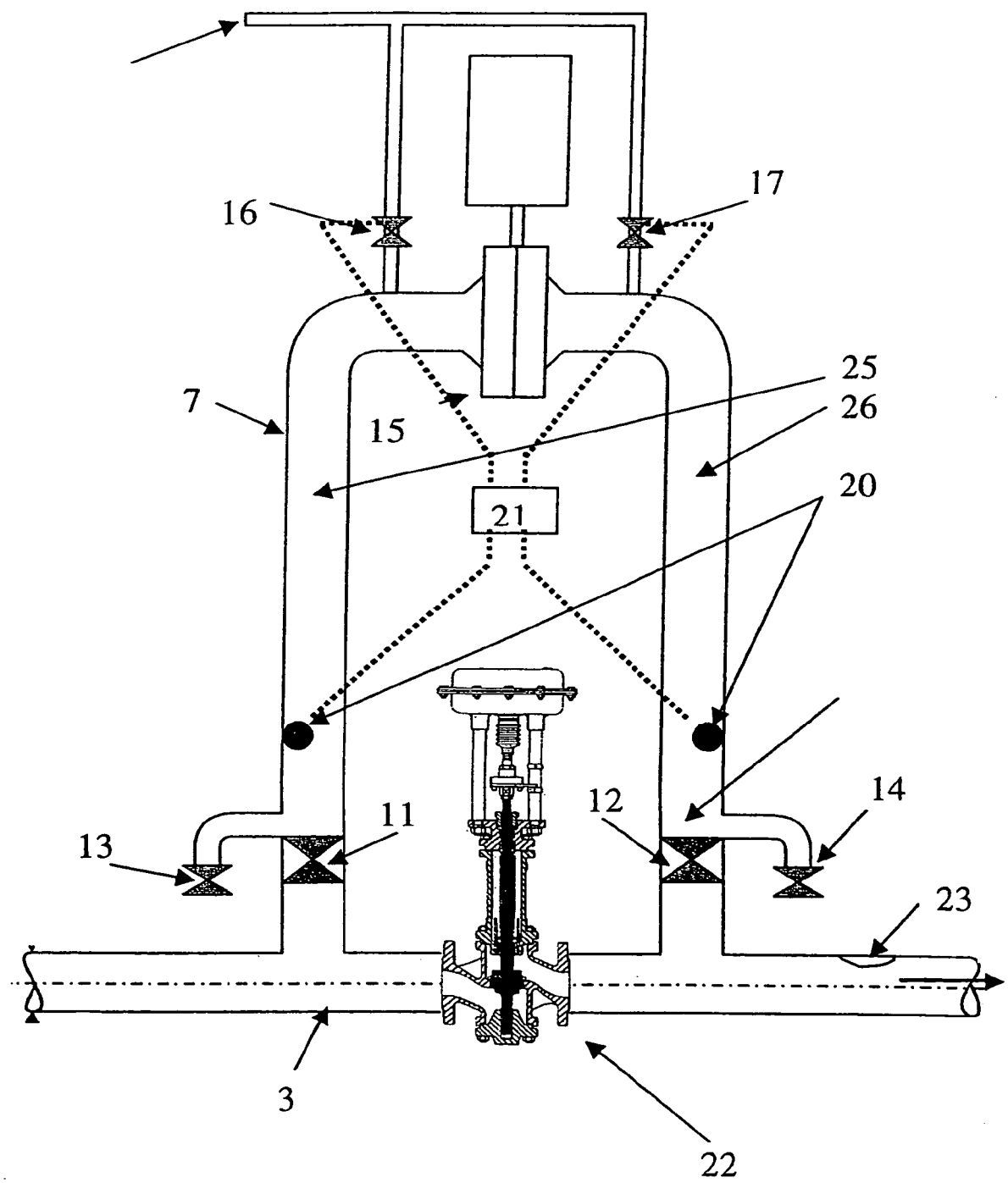
FIG. 6 illustrates a variant of the device.

In the liquid conduit 3, a fourth isolating valve 22 is incorporated in the section 8 which is bridged over by the bypass conduit 7, which fourth isolating valve blocks the main flow, i.e. the liquid flow that is routed via the liquid conduit 3 to the filling machines 4 or the like. The valve 22 is configured either as an isolating valve (FIG. 2) or as a control valve such as illustrated in FIG. 6. In one embodiment as an isolating valve, realized as a plug valve, for instance, the slide valve is preferably provided with a hole, wherein the hole has a diameter ranging, e.g., from a few millimeters to 20 mm. In this way, a slight onward flow of the medium flowing in the liquid conduit is ensured, even if the valve is closed. The hole thus forms a leakage opening leaving open a passage for the flow. Furthermore, a throttle 23 is incorporated in the liquid conduit in the flow direction after the bypass conduit 7.

The functioning of the device 6 according to the invention is as follows:

During the normal conveyance of liquid 24 (FIG. 3) via the liquid conduit 3, the first and the second isolating valves 11, 12 are open and the pet cocks 13, 14 are closed. In the bypass conduit 7 in which the third isolating valve 15 is closed, gas cushions are present in the two spaces 25, 26 which are formed by the closed third valve, namely in such a manner that the liquid level 27 is below the probes 20 provided in those spaces 25, 26. During the conveyance of the liquid 24, the fourth isolating valve 22 is open. Should pressure surges or high-frequency pressure variations occur, those will be absorbed or reduced, respectively, by the gas cushions present in the two gas-filled spaces 25, 26 of the bypass conduit 7.

$CO_2$ or sterile air is preferably used for the production of a gas cushion.

Figure 3:
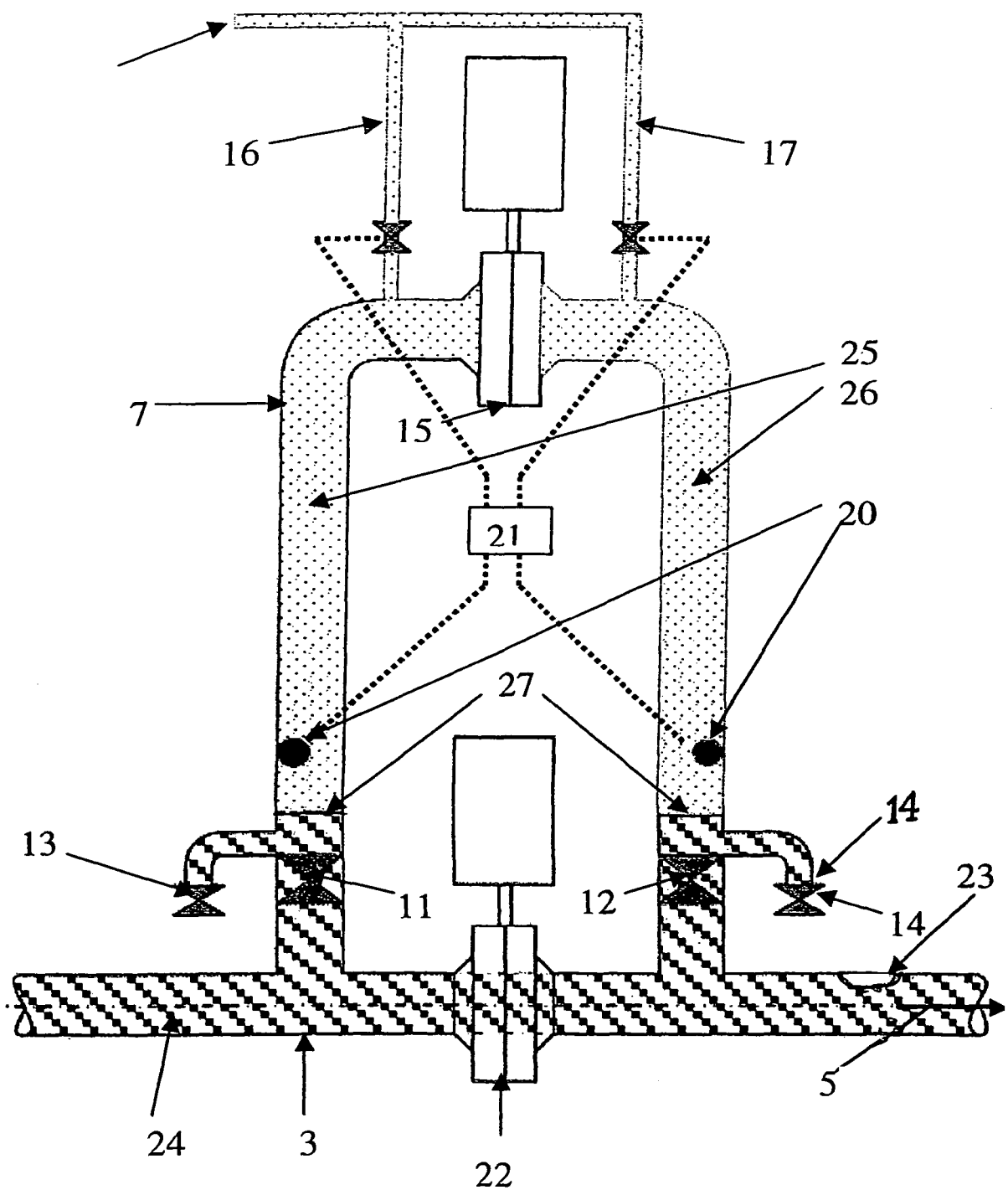
FIGS. 3 to 5 show various operating conditions of the device according to the invention.

The gas pressure of the gas cushions is adapted to the prevailing static operating pressure of the liquid in such a way that the liquid level 27 will always remain below the probes 20. This condition is illustrated in FIG. 3.

Figure 4:
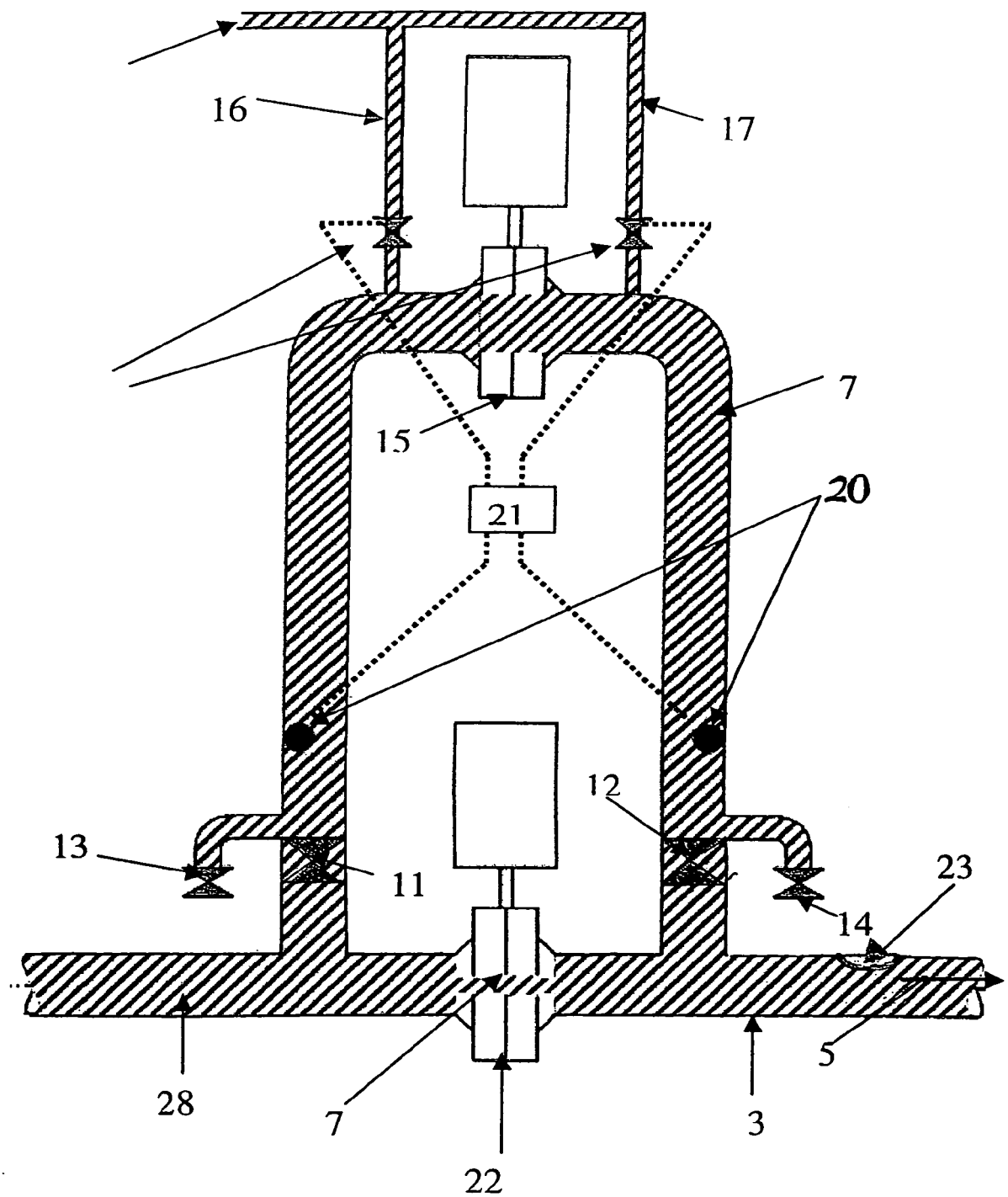
Figure 5:
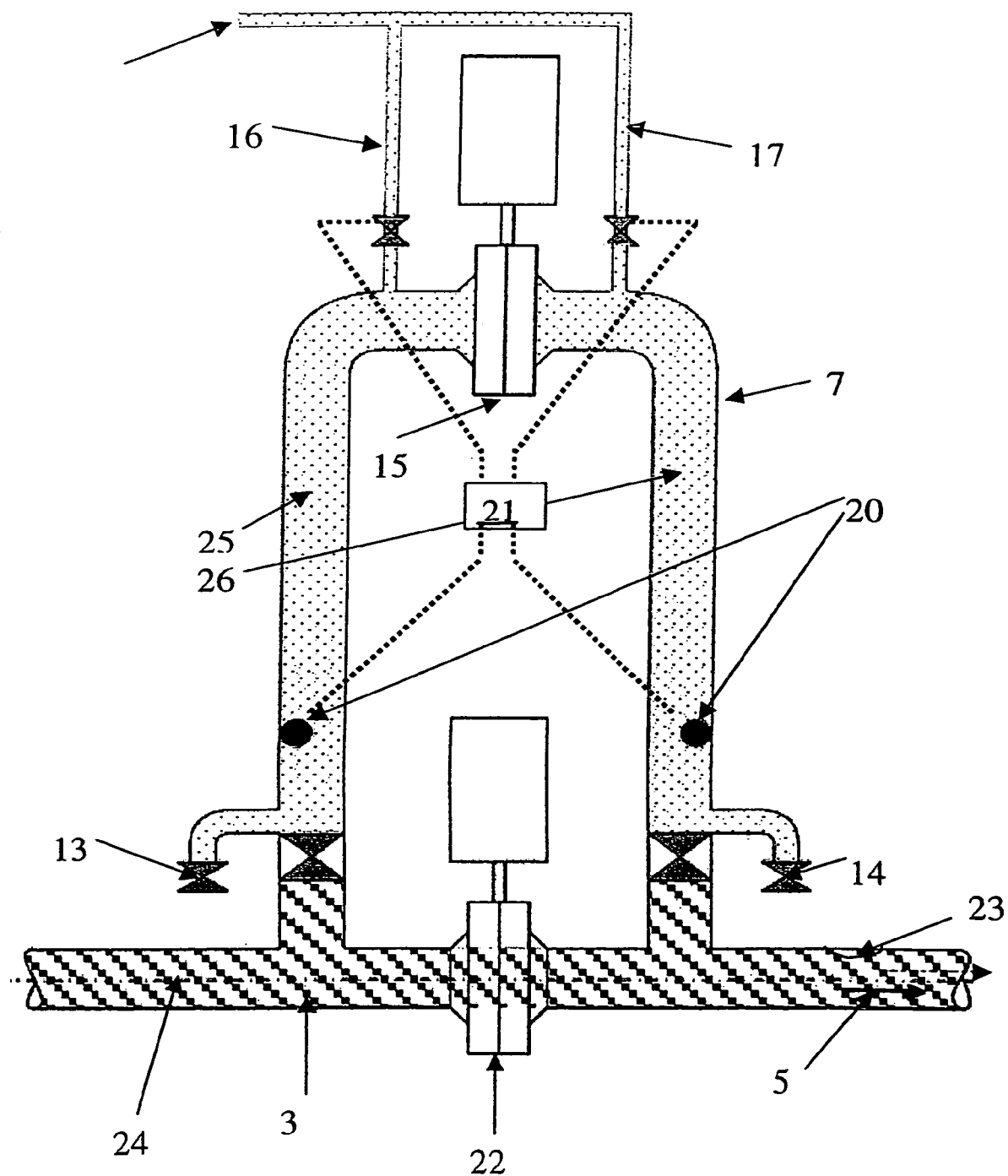

For the purpose of cleaning (FIG. 4) the liquid conduit 3, the first and the second isolating valves 11, 12 remain open; however, the third isolating valve 15 is opened and the fourth isolating valve 22 is closed. The two pet cocks 13, 14 are temporarily opened or supplied with clock pulses, respectively, in order to likewise remove the previously conveyed liquid 24 from the pipeline portions leading from the bypass conduit 7 to the pet cocks 13, 14 and in order to fill and flush through those pipelines with a cleaning medium 28. The gas supply conduits are also temporarily opened or supplied with clock pulses (cf. FIG. 4).

As a result of the leakage opening of the isolating valve 22 or of an incompletely closed isolating valve according to FIG. 6, respectively, both the liquid conduit 3 and the bypass conduit 7 are passed through by the cleaning medium. The throttle 23 provides for an absorption of pressure surges in liquid flows or in water flowing thereafter.

Instead of simultaneously flowing through the liquid conduit 3 and the bypass conduit 7, it is also possible to alternatively open and close the isolating valves 15 and 22 during the cleaning cycle in a pulsating fashion so that the cleaning medium will flow, in a pulsating way, through the conduits 3 and 7 in batches.

In order to be able to carry out a product change, i.e., for instance, to completely remove the cleaning liquid, the first and the second isolating valves 11, 12 are first of all closed, the pet cocks 13, 14 are opened and the section between the first and the second isolating valves 11, 12 of the bypass conduit 7 is flooded with gas. Thereby, the third isolating valve 15 is suitably closed. The fourth isolating valve 22 is opened so that the liquid now freshly flowing in through the liquid conduit after the cleaning liquid will displace the same. Upon removal of the cleaning liquid, the first and the second isolating valves 11, 12 are opened and the pet cocks 13, 14 are closed so that the normal condition as illustrated in FIG. 3 will be restored while conveying the liquid via the liquid conduit 3. An analogue procedure is followed if the conveyance changes from one product liquid to another product liquid.

From the charts of FIGS. 7 to 10, it can be seen to what extent pressure surges can be attenuated by means of the device according to the invention. FIG. 7, for instance, shows an attenuated pressure surge during a normal stop of the liquid transport, i.e. involving an electronic attenuation, and FIG. 8 shows the pressure pattern also during a normal stop, however, without the device 6 according to the invention. It is not only possible to detect a markedly higher maximum pressure but also a high frequency of the slowly decaying pressure oscillations resulting in an enormous strain on the entire plant.

FIGS. 9 and 10 show similar charts regarding an instantaneous or emergency stop, respectively, of the liquid to be conveyed, namely FIG. 9 with a device 6 according to the invention and FIG. 10 without a device 6 according to the invention.

The invention is not limited to the exemplary embodiments as illustrated in the drawing but can be modified in various respects. For instance, any pipeline departing from a point of the liquid conduit 3 and running into the liquid conduit 3 at another point or optionally also a pipeline system fulfilling the same function is conceived as a bypass conduit. Likewise, also the liquid conduit 3 can be constructed as a pipeline system.

The invention claimed is:

1. A device for attenuating pressure surges of liquids flowing inside a liquid conduit and for cleaning the liquid conduit comprising:
a bypass conduit that bridges over a section of the liquid conduit, wherein a first isolating valve is disposed in the section of the liquid conduit between outlets of the bypass conduit and at least one lockable gas supply conduit is provided in the bypass conduit, and wherein the bypass conduit is divided into two gas-filled spaces by a second isolating valve disposed within the bypass conduit, a separate lockable gas supply conduit running into each of the two spaces, both spaces communicating with the liquid conduit to attenuate pressure surges therein.

2. A device according to claim 1, further comprising a third and fourth isolating valves disposed in the bypass conduit adjacent each outlet of the bypass conduit configured to separate the bypass conduit from the liquid conduit.

3. A device according to claim 2, wherein a pet cock is provided adjacent to each of the third and fourth isolating valves.

4. A device according to claim 1, wherein the first isolating valve provided in the liquid conduit has, in the closed state, a leakage opening enabling a reduced flow.

5. A device according to claim 1, wherein a probe for determining a liquid level is disposed in each space of the bypass conduit.

6. A device according to claim 5, further comprising a control unit coupled to the lockable gas supply conduits configured to initiate an automatic gas flushing when the liquid level reaches a predetermined value to cause a discharge of liquid from the bypass conduit.

7. A device according to claim 1, wherein each of the two gas-filled spaces is capable of being maintained at a different gas pressure using the separate lockable gas supply conduits.

* * * * *